United States Patent
Meglan et al.

(10) Patent No.: US 12,193,765 B2
(45) Date of Patent: *Jan. 14, 2025

(54) GUIDANCE FOR PLACEMENT OF SURGICAL PORTS

(71) Applicant: Covidien LP, Mansfield, MA (US)

(72) Inventors: Dwight Meglan, Westwood, MA (US); Meir Rosenberg, Newton, MA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,354

(22) Filed: Oct. 6, 2023

(65) Prior Publication Data

US 2024/0033014 A1    Feb. 1, 2024

Related U.S. Application Data

(63) Continuation of application No. 16/960,462, filed as application No. PCT/US2019/012815 on Jan. 9, 2019, now Pat. No. 11,806,085.
(Continued)

(51) Int. Cl.
*A61B 34/20* (2016.01)
*A61B 17/00* (2006.01)
(Continued)

(52) U.S. Cl.
CPC .......... *A61B 34/20* (2016.02); *A61B 17/3403* (2013.01); *A61B 17/3423* (2013.01);
(Continued)

(58) Field of Classification Search
CPC ......... A61B 2090/3612; A61B 2090/363–368; A61B 2090/371; A61B 2090/372;
(Continued)

(56) References Cited

U.S. PATENT DOCUMENTS 3,027,710 A   4/1962  Maytner
7,567,833 B2  7/2009  Moctezuma De La Barrera et al.
(Continued)

FOREIGN PATENT DOCUMENTS

JP    2014117499 A    6/2014
JP    2014525765 A    10/2014
(Continued)

OTHER PUBLICATIONS

Extended European Search Report dated Aug. 4, 2021 corresponding to counterpart Patent Application EP 19738490.2.
(Continued)

*Primary Examiner* — Carolyn A Pehlke
(74) *Attorney, Agent, or Firm* — Carter, DeLuca & Farrell LLP

(57) ABSTRACT

Systems for guiding placement of surgical ports on a body include an image capture device configured to capture an image of an operating environment and generate image data based on the captured image, a display device, and a computing device configured to obtain information regarding a location of a surgical site within the body, receive the image data from the image capture device, generate graphical guidance for placing a surgical port on the body based on the location of the surgical site within the body and the image data, and cause the display device to display the generated graphical guidance.

18 Claims, 6 Drawing Sheets

Related U.S. Application Data

(60) Provisional application No. 62/615,481, filed on Jan. 10, 2018.

(51) Int. Cl.

| | | |
|---|---|---|
| *A61B 17/34* | (2006.01) | |
| *A61B 34/00* | (2016.01) | |
| *A61B 34/10* | (2016.01) | |
| *A61B 34/30* | (2016.01) | |
| *A61B 90/00* | (2016.01) | |

(52) U.S. Cl.
CPC .............. *A61B 34/10* (2016.02); *A61B 34/25* (2016.02); *A61B 90/37* (2016.02); *A61B 2017/00207* (2013.01); *A61B 2034/105* (2016.02); *A61B 2034/2055* (2016.02); *A61B 2034/2065* (2016.02); *A61B 2034/256* (2016.02); *A61B 2034/301* (2016.02); *A61B 2090/365* (2016.02); *A61B 2090/372* (2016.02)

(58) Field of Classification Search
CPC . A61B 2090/373; A61B 90/36; A61B 90/361; A61B 90/37; A61B 2034/252; A61B 2034/254; A61B 2034/256; A61B 2034/258; A61B 34/20; A61B 34/25; A61B 34/30
See application file for complete search history.

(56) References Cited

U.S. PATENT DOCUMENTS

| | | |
|---|---|---|
| 9,737,366 B2 | 8/2017 | Miyamoto |
| 11,806,085 B2 | 11/2023 | Meglan et al. |
| 2003/0109780 A1 | 6/2003 | Coste-Maniere et al. |
| 2014/0148816 A1 | 5/2014 | McDonald et al. |
| 2014/0362199 A1 | 12/2014 | Popovic et al. |
| 2015/0366628 A1 | 12/2015 | Ingmanson |
| 2016/0166333 A1 | 6/2016 | Wang et al. |
| 2017/0186157 A1 | 6/2017 | Boettger et al. |
| 2017/0312035 A1 | 11/2017 | May et al. |
| 2019/0069962 A1 | 3/2019 | Tabandeh et al. |

FOREIGN PATENT DOCUMENTS

| | | |
|---|---|---|
| JP | 2015504689 A | 2/2015 |
| JP | 2018511359 A | 4/2018 |
| WO | 2016133644 A1 | 8/2016 |
| WO | 2017151904 A1 | 9/2017 |

OTHER PUBLICATIONS

International Search Report dated May 2, 2019 and Written Opinion completed May 1, 2019 corresponding to counterpart Int'l Patent Application PCT/US2019/012815.

U.S. Appl. No. 62/615,495, entitled "Guidance for Positioning a Patient and Surgical Robot", filed Jan. 10, 2018.

Japanese Office Action dated Feb. 6, 2023 corresponding to counterpart Patent Application JP 2020-538103.

Office Action dated Jun. 4, 2023 for Chinese Patent Application No. 2019800102330 (17 pages).

GUIDANCE FOR PLACEMENT OF SURGICAL PORTS

CROSS-REFERENCE TO RELATED APPLICATIONS

This application is a Continuation application which claims the benefit of and priority to U.S. patent application Ser. No. 16/960,462, filed Jul. 7, 2020, (now U.S. Pat. No. 11,806,085) which is a National Stage Application of PCT Application Serial No. PCT/US2019/012815 under 35USC § 371 (a), filed Jan. 9, 2019, which claims benefit of and priority to U.S. Provisional Patent Application Ser. No. 62/615,481 filed Jan. 10, 2018, the disclosures of each of the above-identified applications are hereby incorporated by reference in their entirety.

BACKGROUND

Robotic surgery enables surgeons to perform various surgical procedures that would not be possible, or would be less efficient, by manual surgical techniques, such as open and/or laparoscopic surgical procedures. However, for surgeons to be comfortable using the surgical robot for robotic surgical procedures, precise placement of surgical ports is required to ensure that robotic surgical tools have access to a surgical site. Accurately placing surgical ports depends on various factors, including the location of the surgical site, the type of condition being treated, characteristics of the patient, and the type of surgical procedure being performed. Thus, extensive training and preparation is often required for surgeons to learn the best locations to place surgical ports, and how to adjust those locations based on the above-noted factors. Disclosed hereinbelow are improved systems, methods, and computer-readable media for providing guidance for placing surgical ports.

SUMMARY

The present disclosure relates to the provision of guidance for placing surgical ports on a patient's body, and more particularly, to systems, methods, and computer-readable media for generating and displaying virtual or augmented reality visual guidance to guide and/or assist clinicians during planning for and placing of surgical ports on a patient's body.

Provided in accordance with embodiments of the present disclosure are systems for guiding placement of surgical ports on a body. In an aspect of the present disclosure, the system includes an image capture device configured to capture an image of an operating environment including a body and generate image data based on the captured image, display device worn by a user, and a computing device including a processor and a memory storing instructions which, when executed by the processor, cause the computing device to obtain information regarding a location of a surgical site within the body, receive the image data from the image capture device, generate graphical guidance for placing a surgical port on the body based on the location of the surgical site within the body and the image data, and cause the display device to display the generated graphical guidance.

In another aspect of the present disclosure, the instructions, when executed by the processor, further cause the computing device to detect, based on the image data received from the image capture device, that the surgical port has been placed on the body, generate graphical guidance for inserting an endoscope through the surgical port into the body, and detect that the endoscope has been inserted through the surgical port.

In a further aspect of the present disclosure, the detecting that the surgical port has been placed on the body includes analyzing additional image data received from the image capture device to detect that the surgical port has been placed on the body.

In another aspect of the present disclosure, the detecting that the endoscope has been inserted through the surgical port includes analyzing additional image data received from the image capture device to detect that the endoscope has been inserted through the surgical port.

In yet another aspect of the present disclosure, the surgical port is a first surgical port, and the instructions, when executed by the processor, further cause the computing device to generate graphical guidance for placing a second surgical port on the body based on the location of the surgical site within the body and a detected location where the first surgical port has been placed on the body, and cause the display device to display the generated graphical guidance.

In still another aspect of the present disclosure, the generated graphical guidance includes a virtual surgical port displayed on the body, and the instructions, when executed by the processor, further cause the computing device to analyze additional image data received from the image capture device to detect movement of a hand of the user, determine, based on the detected movement of the user's hand, that the user is adjusting a pose of the virtual surgical port on the body, and update the graphical guidance based on the determined adjustment of the pose of the virtual surgical port on the body.

In a further aspect of the present disclosure, the instructions, when executed by the processor, further cause the computing device to provide an alert when the determined adjustment of the pose of the virtual surgical port on the body is more than a predetermined distance or change in orientation from the pose recommended by the graphical guidance.

In another aspect of the present disclosure, detecting movement of the user's hand includes detecting a gesture performed by the user's hand.

In a further aspect of the present disclosure, determining that the user is adjusting the pose of the virtual surgical port on the body is further based on the detected gesture performed by the user's hand.

In another aspect of the present disclosure, the image capture device is coupled to the display device.

In yet another aspect of the present disclosure, the graphical guidance includes textual instructions displayed by way of the display device.

In still another aspect of the present disclosure, the graphical guidance includes an augmented reality image of a recommended pose of the surgical port.

In a further aspect of the present disclosure, the recommended pose of the surgical port is determined based on a predetermined model of recommended surgical port placements.

In another aspect of the present disclosure, the recommended pose of the surgical port is determined based on a predetermined treatment plan.

In yet another aspect of the present disclosure, the recommended pose of the surgical port is determined based on a scan of the body.

In still another aspect of the present disclosure, the graphical guidance includes an augmented reality image of the surgical site within the body.

In a further aspect of the present disclosure, the computing device causes the display device to display the augmented reality image of the surgical site within the body as superimposed onto the body.

In another aspect of the present disclosure, the augmented reality image of the surgical site includes a position of at least one organ within the body.

In a further aspect of the present disclosure, the position of the at least one organ within the body is based on a predetermined model of positions of organs.

In another aspect of the present disclosure, the system further includes a surgical robot including one or more robotic assemblies including a base, a first joint, a first arm coupled to the first joint, a second joint coupled to the first arm and a second arm coupled to the second joint, and the base is coupled to the second arm by way of the first joint, first arm, and second joint.

In a further aspect of the present disclosure, the instructions, when executed by the processor, further cause the computing device to generate graphical guidance for placing the surgical robot based on the determined position of the surgical site within the body.

In yet another aspect of the present disclosure, the instructions, when executed by the processor, further cause the computing device to determine a range of motion of the surgical robot based on the placement of the surgical port on the body, and cause the display device to display an indication of the range of motion of the surgical robot.

In a further aspect of the present disclosure, the range of motion of the surgical robot is determined based on a characteristic of the surgical robot.

In yet a further aspect of the present disclosure, the characteristic of the surgical robot includes one or more of a configuration of the surgical robot, a pose of the surgical robot relative to the body, and a type of tool coupled to the surgical robot.

In another aspect of the present disclosure, the image capture device is a first image capture device, and the system further comprises a second image capture device, and the instructions, when executed by the processor, further cause the computing device to generate a three-dimensional scene of the operating environment based on image data received from the first and second image capture devices.

In a further aspect of the present disclosure, the first and second image capture devices are positioned about the operating environment.

In another aspect of the present disclosure, the image capture device is included in the computing device.

In yet another aspect of the present disclosure, the computing device is included in the display device.

In still another aspect of the present disclosure, the obtaining information regarding a location of the surgical site within the body includes receiving a selection of the surgical site via input from a user.

In yet another aspect of the present disclosure, the obtaining information regarding a location of the surgical site within the body includes determining the location of the surgical site based on image data acquired during a scan of the body.

In still another aspect of the present disclosure, the obtaining information regarding a location of the surgical site within the body includes determining the location of the surgical site based on a predetermined treatment plan.

In yet another aspect of the present disclosure, the instructions, when executed by the processor, further cause the computing device to determine a position of the surgical site within the body based on the received image data.

In still another aspect of the present disclosure, the body is at least a portion of a mannequin.

In yet another aspect of the present disclosure, the body is at least a portion of a patient.

Provided in accordance with embodiments of the present disclosure are methods for guiding placement of surgical ports on a body. In an aspect of the present disclosure, the method includes obtaining information regarding a location of a surgical site within the body, receiving image data, generated based on an image of the operating environment, from an image capture device, generating graphical guidance for placing a surgical port on the body based on the location of the surgical site within the body and the image data, and displaying the generated graphical guidance.

Provided in accordance with embodiments of the present disclosure are non-transitory computer-readable storage media including instructions which, when executed by a computer, cause the computer to obtain information regarding a location of a surgical site within the body, receive image data generated based on an image of an operating environment from an image capture device, generate guidance for placing a surgical port on the body based on the location of the surgical site within the body and the image data, and cause a display device to display the generated graphical guidance.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

The present disclosure is directed to systems, methods, and computer-readable media for providing guidance for placing surgical ports on a patient's body (or, in some examples, a non-human body—such as a mannequin, a virtual body, and the like—that is modeled based upon the patient's body or of another test subject) (referred to collectively hereinafter as a "body"). More particularly, the present disclosure relates to instructing a user, such as a surgeon, nurse, technician, and/or other operating room staff (hereinafter referred to as a clinician or user), how and where to place surgical ports on the body to ensure suitable access for surgical tools coupled to a surgical robot to a surgical site within the body. Various forms of visual and/or auditory guidance may be displayed and/or emitted by one or more display devices, such as a head-mounted display, for example, an augmented reality headgear and/or virtual reality headgear. In some embodiments, the display devices may be one or more projectors or other light emitters coupled to one or more robotic arms of the surgical robot and/or other mount or assembly about the surgical environment, the display devices being configured to display guidance and/or illuminate one or more parts of the body. The guidance may include one or more commands directing the clinician to place surgical ports at particular locations on the body and enable the clinician to adjust the locations of the surgical ports. Thus, the systems, methods, and computer-readable media disclosed herein may be used during training for robotic surgery and/or during actual robotic surgical procedures to assist the clinician with preparing for robotic surgery.

Figure 1:
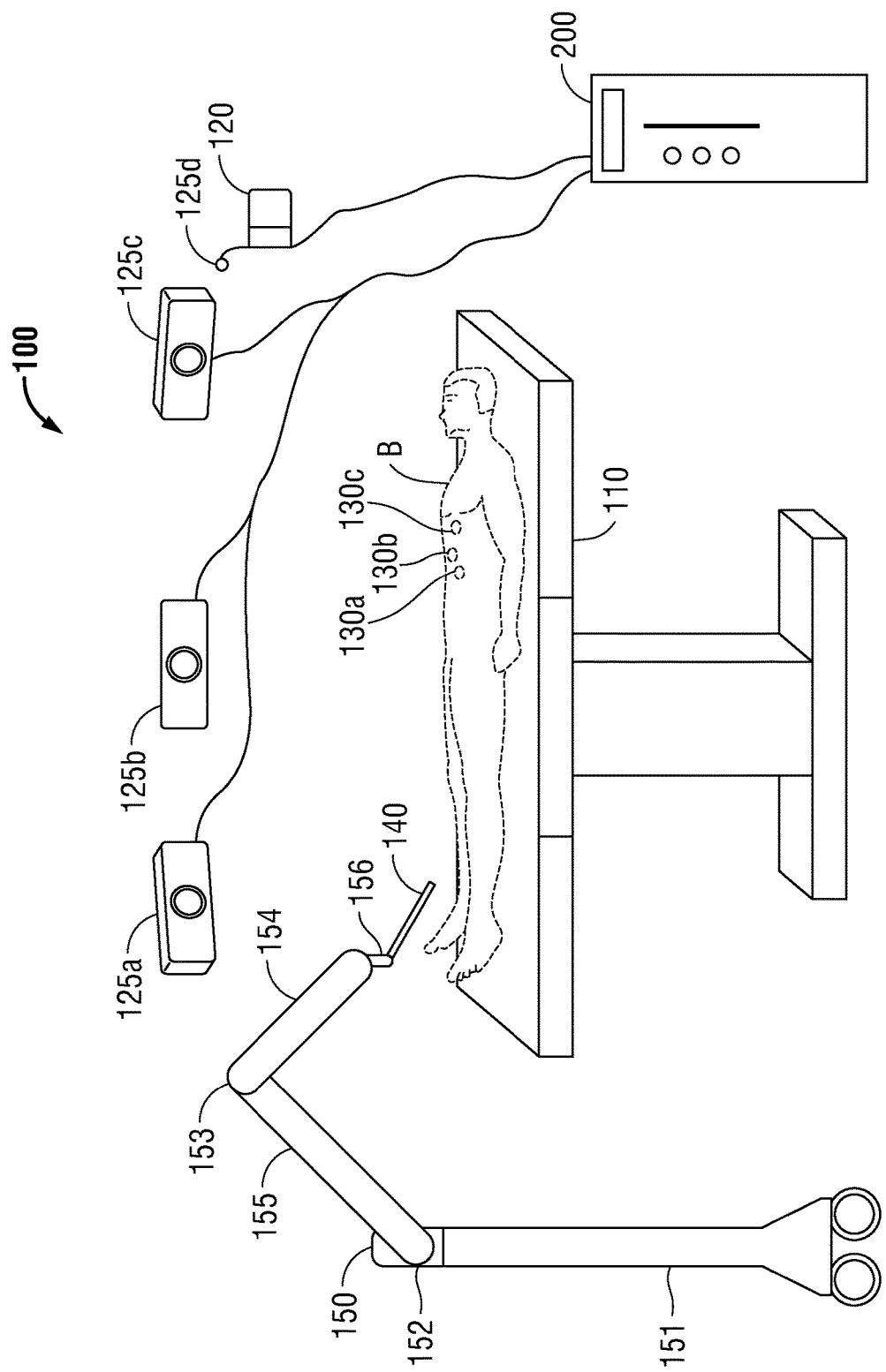
FIG. 1 is a schematic diagram of a system for providing guidance for placing surgical ports, according to an embodiment of the present disclosure.

With reference to FIG. 1, there is shown a system 100 for providing guidance for placing surgical ports, according to an embodiment of the present disclosure. System 100 may include a table 110 capable of supporting a body B, a head-mounted display device (HMD) 120, one or more image capture devices 125a, 125b, 125c, and 125d, one or more surgical ports 130a, 130b, 130c, and 130d, a surgical robot assembly 150, a laparoscope 140, and a computing device 200. Image capture devices 125a, 125b, 125c, and 125d may be any image capture devices known to those skilled in the art, such as video cameras, still cameras, stereoscopic cameras, three-dimensional depth cameras, LIDAR sensors, and/or the like, and may be positioned about an operating environment. As used herein, the term "operating environment" refers to a setting, room, or scene where robotic surgery is performed. As such, the operating environment includes table 110, HMD 120, and one or more image capture devices 125a, 125b, 125c, and 125d. In some embodiments, the operating environment further includes body B on table 110, one or more surgical ports 130a, 130b, 130c, and 130d, surgical robot assembly 150, and/or laparoscope 140. In other embodiments, system 100 may be used in training and/or planning procedures, some or all of body B, surgical ports 130a, 130b, 130c, and 130d, surgical robot assembly 150, and/or laparoscope 140 may not be present in the operating environment. During such training and/or planning procedures, body B may be a virtual or non-human body, as further described below.

One or more images of the capture devices 125a, 125b, 125c, and 125d, for example image capture device 125d as shown in FIG. 1, may be included in or coupled to HMD 120. Additionally, or alternatively, image capture devices 125a, 125b, 125c, and 125d may be coupled or otherwise connected, whether by wireless or wired connection, to computing device 200. Image capture devices 125a, 125b, 125c, and 125d are referred to collectively hereinafter as image capture devices 125. Surgical ports 130a, 130b, 130c, and/or 130d may be any port or device usable for inserting surgical tools into body B, such as trocars. Surgical ports 130a, 130b, 130c, and 130d are referred to collectively hereinafter as surgical ports 130.

Surgical robot assembly 150 may include a base 151, a first joint 152 coupled to base 151, a first robotic arm 155, coupled to first joint 152, a second joint 153 coupled to first robotic arm 155, a second robotic arm 154 coupled to second joint 153, and an instrument drive unit 156 coupled to second arm 154. Laparoscope 140 may be attached to surgical robot assembly 150 via instrument drive unit 156. In embodiments, surgical robot assemblies 150 may be used concurrently and may together form a surgical robot. While a single surgical robot assembly 150 is shown in FIG. 1, multiple surgical robot assemblies 150 may be included in the surgical training environment, and those skilled in the art will recognize that the below-described methods may be applied to surgical robots having single and/or multiple surgical robot assemblies 150, each including at least one base 151, robotic arms 154 and 155, joints 152 and 153, and instrument drive unit 156, without departing from the scope of the present disclosure.

Those skilled in the art will recognize that system 100 may also include other display devices in addition to or instead of HMD 120, without departing from the scope of the present disclosure. For example, one or more projectors or other light-emitting devices may be coupled to robotic arms 154 and/or 155, other equipment, lights, or mounts about the surgical environment, etc. Additionally or alternatively, various other augmented-reality enabled devices, such as tablet computer, smart phones, etc. may also be included in system 100. As such, while HMD 120 is used herein as an illustrative embodiment, the present disclosure is not intended to be limited to having only HMD 120 as a display device.

Body B may be a human body, such as a body of a patient undergoing a surgical procedure, a non-human body, such as a mannequin, physical mock-up, or other simulated body, and/or a virtual body, which, in some cases is modeled based upon a human body of the patient or of a test subject. For example, in embodiments where body B is a virtual body, body B may be generated based on parameters of a particular patient and/or test subject, and may be stored in computing device 200 to be loaded during a surgical procedure and/or a training procedure. In embodiments where body B is a virtual body, body B is not physically present on table 110, but is displayed as an augmented and/or virtual reality image via HMD 120, as described further below. Further, in embodiments where body B is a virtual body, table 110 may also be a virtual table generated by computing device 200 and/or HMD 120 and displayed via HMD 120. Thus, the systems and methods of the present disclosure may be used for training as well as real surgical purposes. In embodiments where a different type of display device, such as a tablet or other hand-held computing device, is used, body B and/or other components of system 100 may be displayed using "windowed augmented reality"—that is, the display device may display body B on table 110 when table 110 is within the view displayed by the display device. Further, those skilled in the art will recognize that various other embodiments of using virtual and/or augmented reality to display body B and/or other components of system 100 may be used in addition to or instead of the embodiments described herein without departing from the scope of the present disclosure.

Computing device 200 may be any computing device configurable for use during training for robotic surgery known to those skilled in the art. For example, computing device 200 may be a desktop computer, laptop computer, server and terminal configuration, and/or a control computer for a surgical robot including surgical robot assembly 150, and/or the like. In some embodiments, computing device 200 may be included in HMD 120. As described further below, system 100 may be used during training for robotic surgery, such as training on how to place surgical ports on body B.

Figure 2:
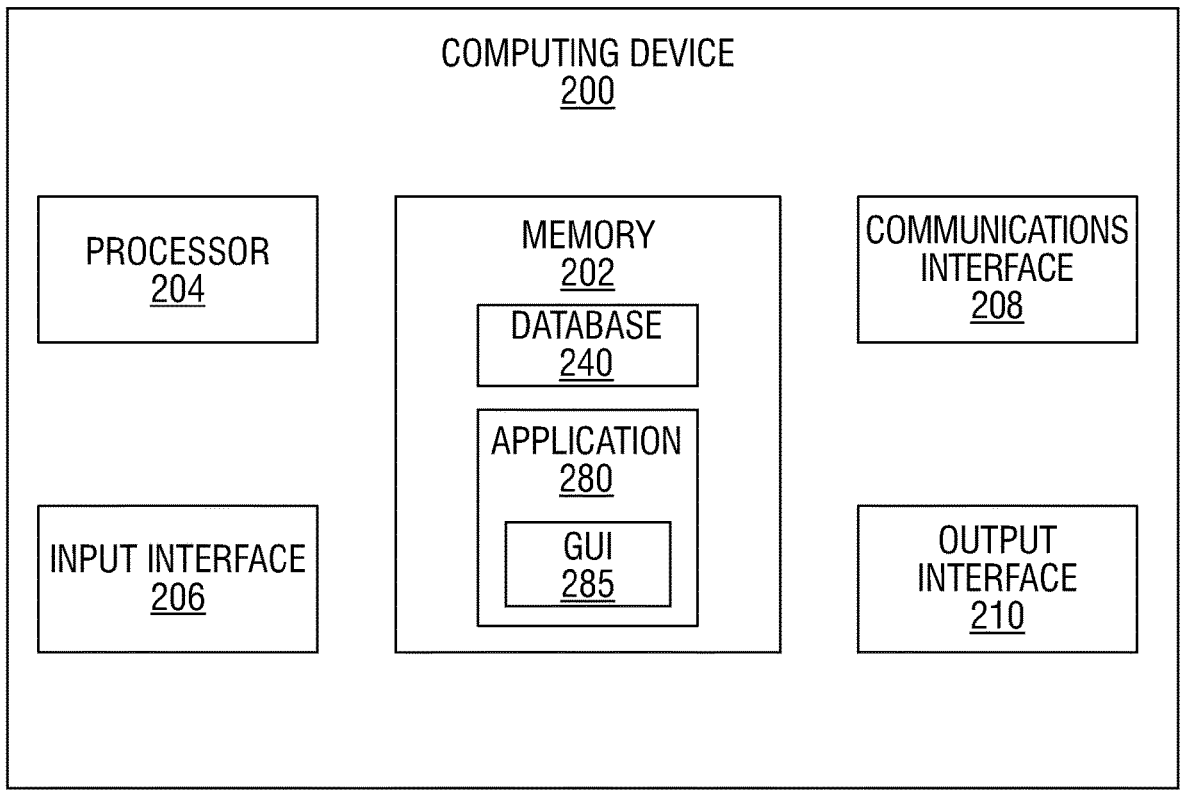
FIG. 2 is a block diagram of an exemplary computing device forming part of the system of FIG. 1.

Turning now to FIG. 2, there is shown a schematic diagram of computing device 200 forming part of system 100 of FIG. 1, according to an embodiment of the present disclosure. Computing device 200 includes a memory 202, a processor 204, an input interface 206, a communications interface 208, and an output interface 210. Memory 202 stores a database 240 and an application 280. Application 280 may include instructions which, when executed by processor 204, cause computing device 200 to perform various functions, as described below. Application 280 further includes graphical user interface (GUI) instructions 285 which, when executed by processor 204, cause computing device 200 to generate one or more GUIs (not shown in FIG. 2), such as, for example, the example GUI 400 shown in FIGS. 4A and 4B. Database 240 may store various scans and/or models of one or more patients' bodies and/or treatment plans for surgical procedures. For example, predetermined and/or patient specific treatment plans may be based on a location of a surgical site and various treatments to be performed at the surgical site.

Memory 202 may include any non-transitory computer-readable storage medium for storing data and/or software that is executable by processor 204 and which controls the operation of computing device 200. In an embodiment, memory 202 may include one or more solid-state storage devices such as flash memory chips. Alternatively, or in addition to the one or more solid-state storage devices, memory 202 may include one or more mass storage devices connected to the processor 204 through a mass storage controller (not shown in FIG. 2) and a communications bus (not shown in FIG. 2). Although the description of computer-readable media included herein refers to a solid-state storage, it should be appreciated by those skilled in the art that computer-readable storage media can be any available media that can be accessed by processor 204. That is, computer-readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 200.

Input interface 206 may be a mouse, keyboard, or other hand-held controller, foot pedal, touch screen, voice interface, and/or any other device or interface by means of which a user may interact with computing device 200. Communications interface 208 may be configured to connect to a network such as a local area network (LAN) consisting of a wired network and/or a wireless network, a wide area network (WAN), a wireless mobile network, a Bluetooth network, and/or the internet. Output interface 210 may be a screen or other display device usable to output images or data by computing device 200.

Figure 3A:
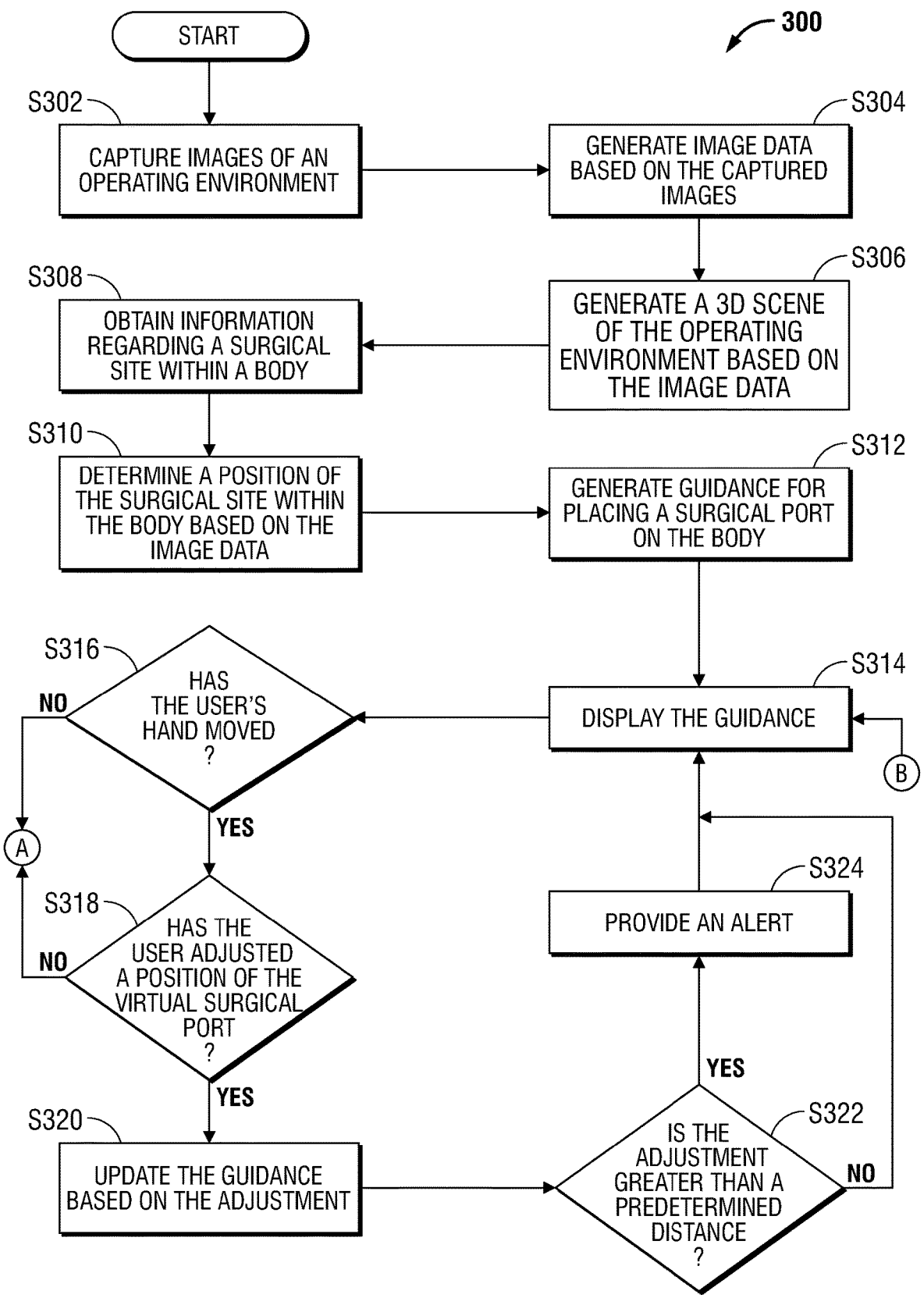
FIGS. 3A and 3B show a flowchart of an exemplary method for providing guidance for placing surgical ports, according to an embodiment of the present disclosure.
Figure 3B:
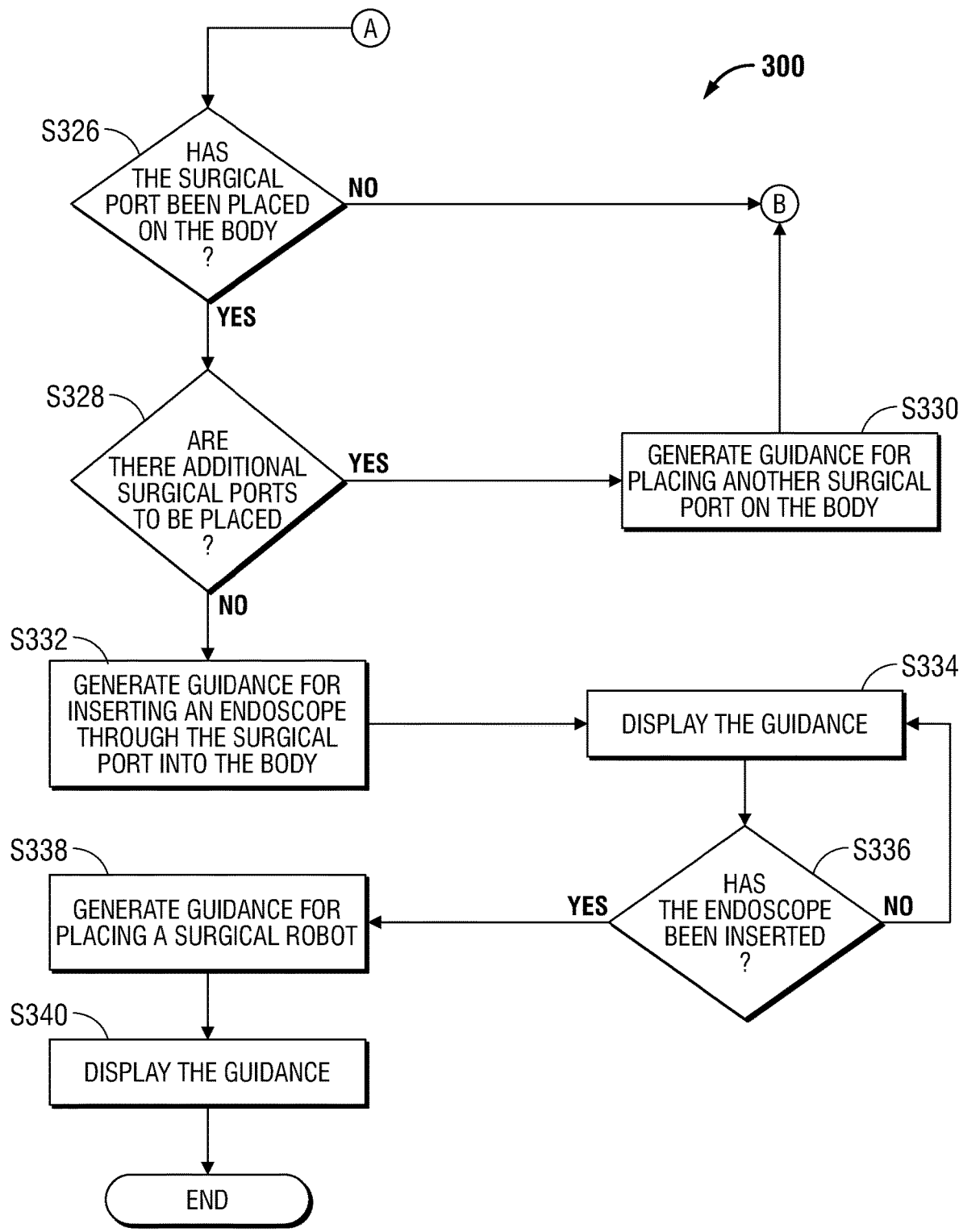

With reference to FIGS. 3A and 3B, there is shown a flowchart of an exemplary method 300 for providing guidance for placing surgical ports, according to an embodiment of the present disclosure. In some embodiments, some or all of the steps of method 300 may be performed in a surgical environment, such as an operating room, prior to the start of a surgical procedure. In other embodiments, some or all of the steps of method 300 may be performed in an instructional environment, such as a training facility where a curriculum is taught. The exemplary embodiments described below are provided purely for illustrative purposes and should not be interpreted as limiting, as those skilled in the art will recognize that many other embodiments are also contemplated within the scope of the present disclosure.

Starting at step S302, one or more image capture devices 125 capture an image of the operating environment. As described above, the operating environment includes table 110 and surgical robot assembly 150. In some embodiments, the operating environment may further include body B on table 110. Image capture devices 125 then, at step S304, generates image data of the operating environment based on the image captured at step S302. Additionally, image capture device 125 may continuously capture images of the operating environment, and thus, even though steps S302 and S304 are shown at the start of method 300, the capturing of images and generating of image data of the operating environment based on the captured images may be a continuous action performed throughout method 300. As such, during some or all of the steps described below, additional images may be captured and additional image data of the operating environment generated and the images and/or image data provided to computing device 200.

Thereafter, at step S306, the image data generated at step S304 is provided to computing device 200. In some embodiments, image capture devices 125 do not generate the image data of the operating environment, but instead provide the captured image to computing device 200, which in turn generates the image data of the operating environment based on the captured image. In such embodiments, it is the captured image that is provided to computing device 200 at step S306 and not the image data of the operating environment. Computing device 200 then processes the image data to generate a three-dimensional (3D) scene of the operating environment. The 3D scene of the operating environment is based on the image data, data received from other sources, and/or input provided by the user.

Computing device 200 then, at step S308, obtains information regarding a surgical site inside body B. The information regarding the surgical site may be provided by the user, such as via input interface 206. In some embodiments, the information regarding the surgical site is preconfigured prior to the start of the surgical procedure. The information regarding the surgical site may include a location within body B where the surgical procedure will be performed, the position and/or type of organs and/or other structures involved in the surgical procedure, and/or the type of surgical procedure that will be performed. For example, the information regarding the surgical site may indicate that the surgical procedure will include removal of a portion of a patient's lung.

Thereafter, at step S310, computing device 200 determines a position of the surgical site within body B. The determination may be based on the information regarding the surgical site received at step S308, radiographic image data of body B, and/or the image data received at step S306. For example, radiographic image data, such as computed tomography and/or magnetic resonance image data of body B, that was acquired prior to the start of the procedure, may be loaded and warped or deformed to match the observed pose of body B as detected in the image data received at step S306 (which will likely not align with the pose of body B when the radiographic image data was acquired). Additionally or alternatively, in a statistical technique, various models of organ positions may be used to estimate locations of organs and other structures within body B, as described further below. The determination may further be based on a treatment plan. For example, in the example described above with reference to step S308, computing device 200 may process the image data to identify body B within the image data, and then identify the position of the surgical site, e.g. the patient's lungs, based on a pose of body B on table 110. As used herein, the term "pose" is defined as a position and an orientation of an object. For example, the pose of body B refers to a position of body B on table 110, an orientation of body B with respect to table 110 and/or the operating environment, as well as other objects in the operating environment. Similarly, a pose of other objects in the operating environment, such as table 110 and surgical robot assembly 150, etc., may also be determined.

Identifying the position of the surgical site within the patient's body may be based on a model of organ locations and locations of other structures within a patient's body. The model of organ locations may be a general model based on data points relating to organ locations received from various patients, or the model of organ locations may be a model generated based on one or more scans and/or other radiographic imaging of the patient being treated.

Computing device 200 then, at step S312, generates guidance for placing a first surgical port 130 on body B. The guidance is generated based on the position of the surgical site within body B, as determined at step S310, and the 3D scene of the operating environment generated at step S306. The guidance may further be based on a model of recommended surgical port placement locations for a particular surgical site and/or a particular type of surgery. Additionally, the guidance may be based on recommended surgical port placement locations included in a predetermined treatment plan. For example, the recommended surgical port placements may be determined based on the dexterous workspace of surgical tools that will be inserted through the surgical ports—that is, the recommended surgical port placement locations may be determined such that the dexterous workspace of the surgical tools inserted through the surgical ports collectively includes the entire surgical site, or at least a predetermined portion thereof.

Figure 4A:
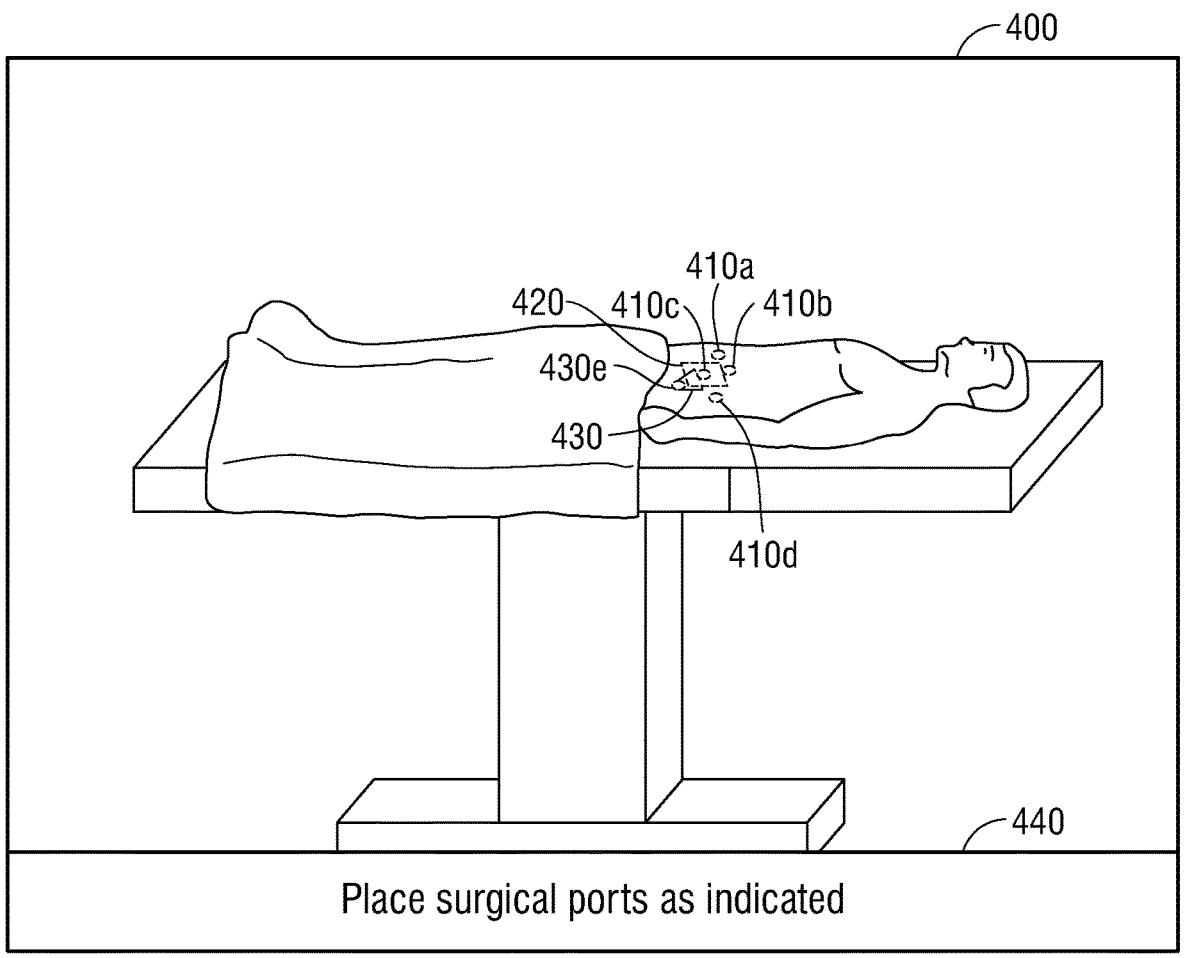
FIG. 4A shows an exemplary graphical user interface that may be displayed by a head-mounted display device forming part of the system of FIG. 1, according to an embodiment of the present disclosure.
Figure 4B:
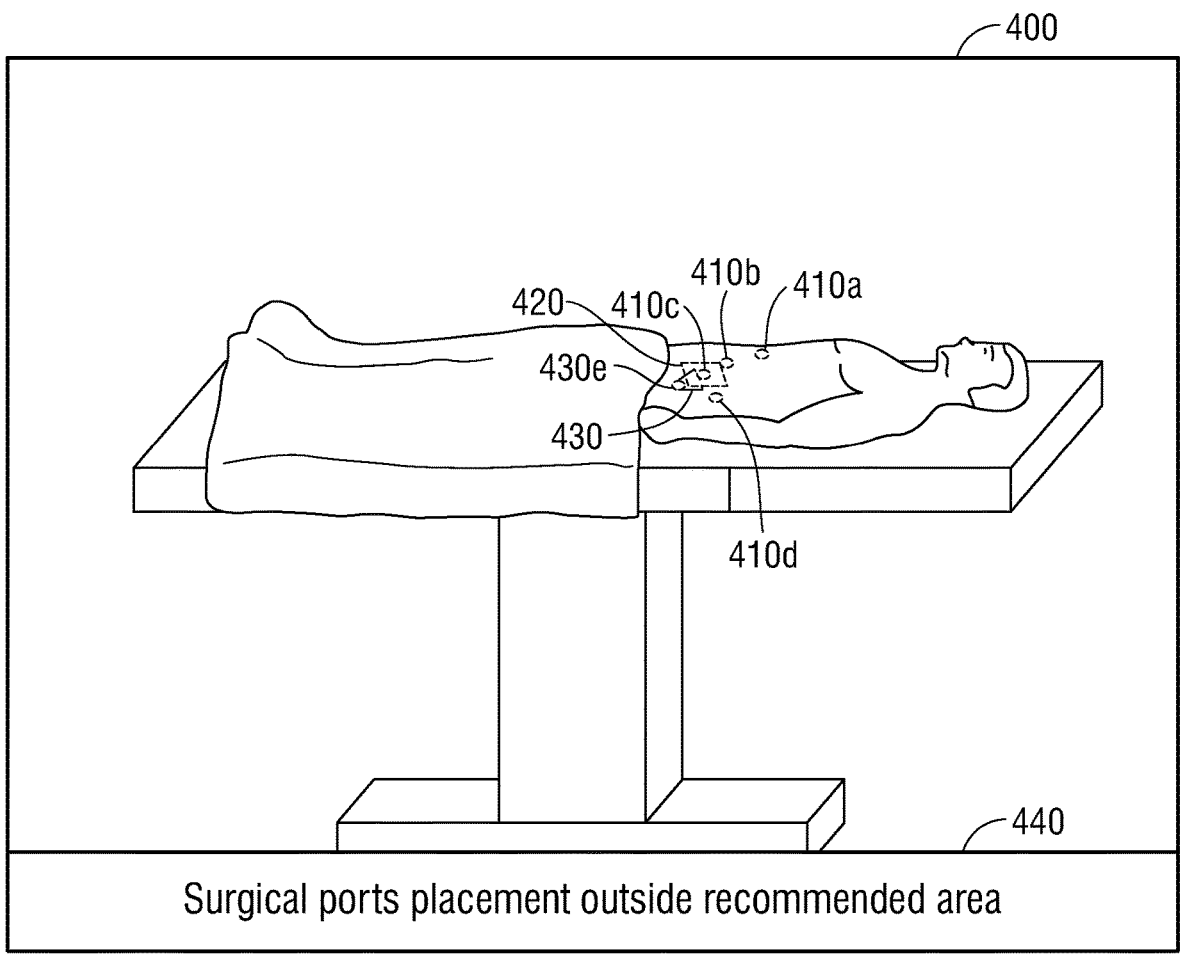
FIG. 4B shows another exemplary graphical user interface that may be displayed by a head-mounted display device forming part of the system of FIG. 1, according to an embodiment of the present disclosure.

In embodiments, the dexterous workspace of the surgical tools is determined based on a bidexterous range of motion of surgical robot assembly 150 and/or robotic arms 154, 155. The determination of the bidexterous range of motion of surgical robot assembly 150 may be based on characteristics of surgical robot assembly 150, including a configuration of surgical robot assembly 150, a pose of surgical robot assembly 150 relative to body B, and/or a type of surgical tool coupled to surgical robot assembly 150. The placement and/or pose of surgical robot assembly 150 about body B may be taken into account when determining the dexterous workspace of the surgical tools, and thus the recommended surgical port placement locations may be determined based on the placement and/or pose of surgical robot assembly 150. Further still, the guidance may be based on recommended surgical port placement locations determined based on a scan of the patient's body. The guidance may be graphical guidance and may include one or more augmented reality images showing the position of the surgical site within body B (as shown in FIGS. 4A and 4B, described below), and a virtual surgical port indicating where the first surgical port 130 should be placed on body B. In other embodiments, the graphical guidance may include images projected onto the patient's body by one or more display devices (e.g. projectors or light-emitting devices). The guidance may further include visual indicators, such as arrows, pointers, etc., as well as textual as well as auditory commands (as shown in, and further described with reference to, FIGS. 4A and 4B) directing the user where to place the surgical ports 130. Computing device 200 then, at step S314 displays the guidance generated at step S312 (as shown in FIG. 4A). In embodiments, computing device 200 may cause HMD 120 to display the guidance, and/or cause other display devices to project the guidance onto body B. For example, computing device 200 may cause HMD 120 to display a virtual representation of the surgical ports 410*a*, 410*b*, 410*c*, 410*d*, 410*e*, the surgical site 420, and/or the dexterous workspace 430 of surgical tools inserted through one or more of surgical ports 410 as an overlay and/or superimposed onto body B, as shown in FIGS. 4A and 4B. In some embodiments, computing device 200 may generate a virtual rendering of an expected view from an endoscope inserted through at least one surgical port 130. The virtual rendering may be generated based on aforementioned models of the surgical site and/or body B. The virtual rendering may be displayed in conjunction with the guidance.

Next, at step S316, computing device 200 determines whether the user has moved, and particularly, whether a hand of the user has moved. The determination may be based on additional image data received by computing device 200 from image capture devices 125. Computing device 200 may process and analyze the additional image data to identify the user and detect whether the user's hand has moved. If it is determined that the user's hand has not moved ("No" at step S316), processing skips ahead to step S326. Alternatively, if it is determined that the user's hand has moved ("Yes" at step S316), proceeds to step S318.

At step S318, computing device 200 determines whether the movement of the user's hand indicates that the user has adjusted a pose of the virtual surgical port displayed as part of the guidance. For example, computing device 200 may process and analyze the additional image data received during step S316 to detect a gesture performed by the user's hand. Various gestures may be performed, for example a pinching gesture, a spreading gesture, a poking gesture, and/or a moving gesture. Various gestures may indicate different actions performed by the user, for example a pinching gesture while the user's hand is directed at a particular virtual surgical port, as displayed by HMD 120, may indicate that the user is selecting or "picking up" the particular virtual surgical port. Likewise, a spreading gesture performed while the user's hand is directed at a particular virtual surgical port, as displayed by HMD 120, may indicate that the user is deselecting or "dropping" the particular virtual surgical port. Similarly, movement of the user's hand while a particular virtual surgical port is selected may indicate that the user is moving the particular virtual surgical port in the direction in which the user's hand is moved. In some embodiments, the user may move a virtual port based on a voice command and/or by eye tracking.

If it is determined that the movement of the user's hand does not indicate that the user has adjusted the pose of the virtual surgical port, or that the user has not given a voice and/or eye tracking command to adjust the pose of the virtual surgical port ("No" at step S318), processing skips ahead to step S326. Alternatively, if it is determined that the movement of the user's hand does indicate that the user has adjusted the pose of the virtual surgical port, or that the user has given a voice and/or eye tracking command to adjust the pose of the virtual surgical port ("Yes" at step S318), processing proceeds to step S320, where computing device 200 updates the guidance based on the adjustment. For example, computing device 200 may adjust the pose of the virtual surgical port from the pose recommended in the guidance generated at step S312 to the pose to which the user moved the virtual surgical port, as determined at step S318.

Thereafter, at step S322, computing device 200 determines whether the adjustment of the virtual surgical port is greater than a predetermined distance or change in orientation from the pose recommended in the guidance generated at step S312. The predetermined distance and orientation may be based on the location of the surgical site within body B and/or the type of surgical procedure being performed. For example, colorectal surgical procedures may require less precise placement of surgical ports, and thus allow the user greater flexibility in placing the surgical ports, while spinal and/or neuro surgical procedures may require more precise placement of surgical ports. If it is determined that the adjustment of the virtual surgical port is greater than the predetermined distance or change in orientation ("Yes" at step S322), processing proceeds to step S324, where an alert is provided to the user to indicate to the user that the pose of the virtual surgical port has been adjusted by more than the predetermined distance from the recommended pose. Thereafter, or if it is determined at step S322 that the adjustment of the virtual surgical port is not greater than the predetermined distance or change in orientation ("No" at step S322), processing returns to step S314, where the guidance, as updated at step S320, is displayed.

At step S326, computing device 200 determines whether the first surgical port 130 has been placed on body B. For example, as described above with reference to step S302, computing device 200 may receive additional image data from image capture devices 125, and may process and analyze the additional image data to determine whether the first surgical port 130 has been placed on body B. If it is determined that the first surgical port 130 has not been placed on body B ("No" at step S326), processing returns to step S314. Alternatively, if it is determined that the first surgical port 130 has been placed on body B ("Yes" at step S326), processing proceeds to step S328, where it is determined whether there are additional surgical ports 130 to be placed on body B. For example, computing device 200 may determine based on the predetermined treatment plan and/or the model of surgical port placement locations, whether additional surgical ports 130 should be placed on body B. Computing device 200 may also receive input from the user indicating whether additional surgical ports 130 should be placed on body B.

If it is determined that there are additional surgical ports 130 to be placed on body B ("Yes" at step S328), processing proceeds to step S330, where computing device 200 generates guidance for placing another surgical port 130 on body B. The guidance may be generated based on the position of the surgical site within body B, as determined at step S310, the 3D scene of the operating environment generated at step S306, and/or the pose of the first surgical port 130 placed on body B. For example, the guidance may include one or more augmented reality images showing the position of the surgical site within body B, and a virtual surgical port indicating where the additional surgical port 130 should be placed on body B. Thereafter, processing returns to step S314, where the guidance is displayed.

Alternatively, if it is determined at step S328 that there are no additional surgical ports 130 to be placed on body B ("No" at step S328), processing proceeds to step S332, where computing device 200 generates guidance for inserting endoscope 140 via at least one surgical port 130 into body B. The guidance may be generated based on the position of the surgical site within body B, the locations where surgical ports 130 were placed on body B, and/or the 3D scene of the operating environment generated at step S306. The guidance may be graphical guidance and may include one or more augmented reality images showing the position of the surgical site within body B, the surgical ports 130 on body B, and an indication of the surgical port 130 into which endoscope 140 should be inserted. The guidance may further include visual indicators, such as arrows, pointers, etc., as well as textual as well as auditory commands. In some embodiments, endoscope 140 is inserted after the first surgical port 130 is place on the body, and thus in such embodiments steps S332, S334, and S336 may be performed prior to step S328.

Thereafter, at step S334, computing device 200 displays the guidance generated at step S332. For example, computing device 200 may cause HMD 120 to display the guidance. Then, at step S336, computing device 200 determines whether endoscope 140 has been inserted via a surgical port 130 into body B. For example, computing device 200 may receive additional image data from image capture devices 125, as described above with reference to step S302, and may process and analyze the additional image data to determine whether endoscope 140 has been inserted via surgical port 130 into body B. If it is determined that endoscope 140 has not been inserted ("No" at step S336), processing returns to step S334. Alternatively, if it is determined that endoscope 140 has been inserted ("Yes" at step S336), processing proceeds to step S338.

At step S338, computing device 200 generates guidance for placing surgical robot assembly 150. For example, computing device 200 may determine a recommended pose for placing surgical robot assembly 150 about body B based on the locations where surgical ports 130 were placed, and the position of the surgical site within body B. Generation of guidance for placing a surgical robot using augmented and/or virtual reality display devices is further described in commonly-owned U.S. Patent Application No. 62/615,495, entitled GUIDANCE FOR POSITIONING A PATIENT AND SURGICAL ROBOT, filed on Jan. 10, 2018, by Covidien LP (now U.S. Patent Publication No. US 2020-0337789), the entire contents of which are incorporated herein by reference.

Thereafter, at step S340, computing device 200 displays the guidance generated at step S330. For example, computing device 200 may cause HMD 120 to display the guidance. Thereafter, processing ends.

While the description above relating to method 300 of FIG. 3 refers to functions being performed by computing device 200, those skilled in the art will understand that such functions may be performed by computing device 200 based on execution of one or more applications, such as application 280, and/or based on dedicated hardware and/or other software included in computing device 200. Thus, while described as being performed by computing device 200, the description of method 300 should not be interpreted as being limited to hardware embodiments.

Turning now to FIGS. 4A and 4B, there is shown an exemplary graphical user interface (GUI) 400 that may be displayed by HMD 120 and/or by one or more other display devices, according to an embodiment of the present disclosure. GUI 400 may be displayed by HMD 120 and/or the other display devices at various points during a surgical procedure, such as the procedure described above with reference to method 300 of FIGS. 3A and 3B. In the embodiment demonstrated in FIG. 4A, table 110 and surgical robot assembly 150 are physical objects in the operating environment shown to the user. Body B is shown lying on table 110. Augmented reality images of virtual surgical ports 410a, 410b, 410c, 410d, and 410e and surgical site 420 may be overlaid onto body B. GUI 400 further includes guidance instructing the user to place surgical ports 130 as indicated by the locations of virtual surgical ports 410a, 410b, 410c, 410d, and 410e on body B. Augmented reality images of an indicator 430 of a bidexterous range of motion of a surgical tool inserted into a surgical port 130 may further be overlaid onto body B. GUI 400 may also include textual instructions 440 to display textual commands to the user.

If the user chooses to adjust the pose of one or more of virtual surgical ports 410a, 410b, 410c, 410d, and 410e, GUI 400 may be updated to indicate the new pose of the virtual surgical ports that have been moved. For example, as shown in FIG. 4B, an updated GUI 400 shows that virtual surgical port 410a has been moved, and that the movement has taken virtual surgical port 410a outside of a recommended range of placements for access to the surgical site. In such an embodiment, textual instructions 440 may provide an alert to the user indicating that virtual surgical port 410a has been adjusted more than a predetermined distance or change in orientation from the pose recommended by the guidance.

As one skilled in the art will appreciate, the systems, methods, and computer-readable media described in the present disclosure describes various aspects of instructing a clinician on how and where to place surgical ports on the body to ensure suitable access for surgical tools coupled to a surgical robot to a surgical site within the body. Various forms of visual and/or auditory guidance may be displayed and/or emitted by one or more display devices, including a head-mounted display and/or projectors or hand-held display devices, such as one or more commands directing the clinician to place surgical ports at particular locations on the body and enable the clinician to adjust the locations of the surgical ports. Thus, the systems, methods, and computer-readable media disclosed herein provide improvements to training and/or preparing for robotic surgical procedures.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure.

What is claimed is:

1. A system for guiding placement of surgical ports on a body, the system comprising:
an image capture device configured to:
capture an image of an operating environment including a body; and
generate image data based on the captured image;
a display device; and
a computing device including a processor and a memory storing instructions which, when executed by the processor, cause the computing device to:
obtain information regarding a location of a surgical site within the body;
receive the image data from the image capture device;
generate graphical guidance for placing a surgical port on the body based on the location of the surgical site within the body and the image data;
cause the display device to display the generated graphical guidance;
detect, based on the image data received from the image capture device, that the surgical port has been placed on the body;
generate graphical guidance for inserting a surgical instrument through the surgical port into the body; and
detect that the surgical instrument has been inserted through the surgical port.

2. The system according to claim 1, wherein the detecting that the surgical port has been placed on the body includes analyzing additional image data received from the image capture device to detect that the surgical port has been placed on the body.

3. The system according to claim 1, wherein the detecting that the surgical instrument has been inserted through the surgical port includes analyzing additional image data received from the image capture device to detect that the surgical instrument has been inserted through the surgical port.

4. The system according to claim 1, wherein the surgical port is a first surgical port, and the instructions, when executed by the processor, further cause the computing device to:
generate graphical guidance for placing a second surgical port on the body based on the location of the surgical site within the body and a detected location where the first surgical port has been placed on the body; and
cause the display device to display the generated graphical guidance.

5. The system according to claim 1, wherein the image capture device is coupled to the display device.

6. The system according to claim 1, wherein the graphical guidance includes textual instructions displayed by way of the display device.

7. The system according to claim 1, wherein the graphical guidance includes an augmented reality image of a recommended pose of the surgical port.

8. The system according to claim 7, wherein the recommended pose of the surgical port is determined based on a predetermined model of recommended surgical port placements.

9. The system according to claim 7, wherein the recommended pose of the surgical port is determined based on a predetermined treatment plan.

10. The system according to claim 7, wherein the recommended pose of the surgical port is determined based on a scan of the body.

11. The system according to claim 1, wherein the graphical guidance includes an augmented reality image of a position of the surgical site within the body.

12. The system according to claim 11, wherein the computing device causes the display device to display the augmented reality image of the position of the surgical site within the body as superimposed onto the body.

13. The system according to claim 12, wherein the augmented reality image of the surgical site includes a position of at least one organ within the body.

14. The system according to claim 13, wherein the position of the at least one organ within the body is based on a predetermined model of positions of organs.

15. A system for guiding placement of surgical ports on a body, the system comprising:
an image capture device configured to:
capture an image of an operating environment including a body; and
generate image data based on the captured image;
a display device; and a computing device including a processor and a memory storing instructions which, when executed by the processor, cause the computing device to:
obtain information regarding a location of a surgical site within the body;
receive the image data from the image capture device;
generate graphical guidance for placing a surgical port on the body based on the location of the surgical site within the body and the image data, wherein the generated graphical guidance includes a virtual surgical port displayed on the body;
cause the display device to display the generated graphical guidance;
analyze additional image data received from the image capture device to detect movement of a user of the system;
determine, based on the detected movement of the user, that the user is adjusting a pose of the virtual surgical port on the body;
update the graphical guidance based on the determined adjustment of the pose of the virtual surgical port on the body; and
provide an alert when the determined adjustment of the pose of the virtual surgical port on the body is more than a predetermined distance or change in orientation from the pose recommended by the graphical guidance.

16. The system according to claim 15, wherein determining that the user is adjusting the pose of the virtual surgical port on the body is further based on a detected gesture performed by a user's hand.

17. A system for guiding placement of surgical ports on a body, the system comprising:
an image capture device configured to:
capture an image of an operating environment including a body; and
generate image data based on the captured image;
a display device; and
a computing device including a processor and a memory storing instructions which, when executed by the processor, cause the computing device to:
obtain information regarding a location of a surgical site within the body;
receive the image data from the image capture device;
generate graphical guidance for placing a surgical port on the body based on the location of the surgical site within the body and the image data;
cause the display device to display the generated graphical guidance;
determine, based on the detected movement of a user, that the user is adjusting a pose of a virtual surgical port displayed on the body;
update the graphical guidance based on the determined adjustment of the pose of the virtual surgical port displayed on the body; and
provide an alert when the determined adjustment of the pose of the virtual surgical port displayed on the body is more than a predetermined distance or is a change in orientation from the pose recommended by the graphical guidance.

18. The system according to claim 17, wherein the instructions, when executed by the processor, further cause the computing device to:
detect, based on the image data received from the image capture device, that the surgical port has been placed on the body;
generate graphical guidance for inserting an instrument through the surgical port into the body; and
detect that the instrument has been inserted through the surgical port.

* * * * *